(12) United States Patent
Zeiner et al.

(10) Patent No.: US 8,758,405 B2
(45) Date of Patent: Jun. 24, 2014

(54) SUTURE TENSIONING DEVICE

(75) Inventors: Mark S. Zeiner, Mason, OH (US);
Mark S. Ortiz, Milford, OH (US)

(73) Assignee: Ethicon Endo-Surgery, Inc, Cincinnati, OH (US)

( * ) Notice: Subject to any disclaimer, the term of this patent is extended or adjusted under 35 U.S.C. 154(b) by 1391 days.

(21) Appl. No.: 11/277,334

(22) Filed: Mar. 23, 2006

(65) Prior Publication Data
US 2007/0225736 A1    Sep. 27, 2007

(51) Int. Cl.
*A61B 17/04*    (2006.01)

(52) U.S. Cl.
USPC .................. 606/232; 606/148; 606/139

(58) Field of Classification Search
USPC ........... 606/148, 139, 232, 151, 103, 74, 300, 606/301, 157, 217; 24/135 N; 411/383
See application file for complete search history.

(56) References Cited

U.S. PATENT DOCUMENTS

| | | | |
|---|---|---|---|
| 3,877,434 A | | 4/1975 | Ferguson et al. |
| 5,084,058 A | * | 1/1992 | Li ................................. 606/148 |
| 5,087,263 A | * | 2/1992 | Li ................................. 606/148 |
| 5,133,723 A | * | 7/1992 | Li et al. ........................ 606/148 |
| 5,281,237 A | | 1/1994 | Gimpelson |
| 5,474,518 A | * | 12/1995 | Farrer Velazquez ........... 600/30 |
| 5,480,405 A | * | 1/1996 | Yoon ............................. 606/139 |
| 5,562,668 A | | 10/1996 | Johnson ..................... 623/13.13 |
| 5,643,289 A | * | 7/1997 | Sauer et al. ................... 606/139 |
| 5,643,295 A | * | 7/1997 | Yoon ............................. 606/151 |
| 5,665,109 A | * | 9/1997 | Yoon ............................. 606/232 |
| 5,669,917 A | * | 9/1997 | Sauer et al. ................... 606/139 |
| 5,725,539 A | * | 3/1998 | Matern .......................... 606/151 |
| 5,752,964 A | * | 5/1998 | Mericle ......................... 606/148 |
| 5,810,853 A | * | 9/1998 | Yoon ............................. 606/151 |
| 5,935,130 A | * | 8/1999 | Kilpela et al. ................. 606/74 |
| 5,984,933 A | * | 11/1999 | Yoon ............................. 606/148 |
| 6,022,360 A | | 2/2000 | Reimels et al. |
| 6,045,561 A | * | 4/2000 | Marshall et al. .............. 606/148 |
| 6,053,921 A | * | 4/2000 | Wagner et al. ................. 606/74 |
| 6,143,005 A | * | 11/2000 | Yoon et al. .................... 606/148 |
| 6,193,754 B1 | * | 2/2001 | Seedhom .................... 623/13.11 |
| 6,221,084 B1 | | 4/2001 | Fleenor |

(Continued)

FOREIGN PATENT DOCUMENTS

| | | |
|---|---|---|
| EP | 1 016 377 A2 | 7/2000 |
| JP | 2001-502190 A | 2/2001 |
| WO | 97/30639 A1 | 8/1997 |

OTHER PUBLICATIONS

Japanese Office Action for Application No. 2007-075145, issued Feb. 28, 2012. (4 pages).

*Primary Examiner* — Corrine M McDermott
*Assistant Examiner* — Jing Ou
(74) *Attorney, Agent, or Firm* — Mintz Levin Cohn Ferris Glovsky and Popeo, P.C.

(57) ABSTRACT

The present invention generally provides devices and methods for tensioning a length of suture. In one embodiment, a suture tensioning device is provided having a shaft and a suture grasping member. A knotting element can be removably coupled to a distal end of the shaft, and it can be adapted to receive a suture and to lock to engage the suture. The suture grasping member can be movably coupled to the shaft and configured to grasp a suture and pull it through the knotting element to allow the knotting element to lock and engage the suture.

23 Claims, 11 Drawing Sheets

(56) References Cited

U.S. PATENT DOCUMENTS

| | | | |
|---|---|---|---|
| 6,306,159 B1* | 10/2001 | Schwartz et al. | 606/232 |
| 6,364,885 B1* | 4/2002 | Kilpela et al. | 606/74 |
| 6,387,041 B1* | 5/2002 | Harari et al. | 600/30 |
| 6,511,488 B1* | 1/2003 | Marshall et al. | 606/148 |
| 6,547,725 B1* | 4/2003 | Paolitto et al. | 600/201 |
| 6,641,597 B2* | 11/2003 | Burkhart et al. | 606/232 |
| 6,656,185 B2* | 12/2003 | Gleason et al. | 606/74 |
| 6,695,852 B2* | 2/2004 | Gleason | 606/103 |
| 7,390,329 B2* | 6/2008 | Westra et al. | 606/151 |
| 2002/0019649 A1* | 2/2002 | Sikora et al. | 606/232 |
| 2002/0072753 A1* | 6/2002 | Cohen | 606/103 |
| 2002/0188297 A1* | 12/2002 | Dakin et al. | 606/72 |
| 2003/0083669 A1* | 5/2003 | Gleason | 606/103 |
| 2003/0120287 A1* | 6/2003 | Gross et al. | 606/148 |
| 2003/0139776 A1* | 7/2003 | Paolitto et al. | 606/232 |
| 2003/0163143 A1* | 8/2003 | Wakabayashi | 606/148 |
| 2003/0167062 A1* | 9/2003 | Gambale et al. | 606/138 |
| 2003/0181926 A1* | 9/2003 | Dana et al. | 606/148 |
| 2003/0220659 A1* | 11/2003 | Schmieding et al. | 606/148 |
| 2004/0097976 A1* | 5/2004 | Hart | 606/148 |
| 2004/0153103 A1* | 8/2004 | Schwartz et al. | 606/148 |
| 2004/0162569 A1* | 8/2004 | Sikora et al. | 606/148 |
| 2004/0230206 A1* | 11/2004 | Gellman et al. | 606/148 |

* cited by examiner

SUTURE TENSIONING DEVICE

FIELD OF THE INVENTION

The invention relates broadly to methods and devices for tensioning a suture.

BACKGROUND OF THE INVENTION

Severe obesity is a major health risk that can decrease life expectancy and give rise to a number of other associated ailments, including the onset of cardiovascular disease, hypertension, diabetes and severe arthritis. A number of surgical procedures can be performed to aid in the treatment of obesity. The most common procedure is a gastric restriction procedure in which opposed gastric walls are fastened or stapled together to effectively reduce the volume of a patient's stomach. More specifically, the stomach is divided by a series of staples or fasteners that extend vertically for about 2.5 inches to create a smaller stomach pouch. The outlet of the pouch into the larger stomach limits the amount of food the stomach can hold and reduces the rate of gastric emptying.

Some gastric restriction procedures utilize a series of fasteners that are coupled by a suture used to cinch and pull the fastened tissue together. Suture-coupled fasteners offer the advantage of allowing the surgeon to adjust the tension of the sutures, if necessary, whereas staples must be removed and reapplied. In particular, because the stomach is resilient and tends to stretch to return to its original state, it is often necessary to re-create the gastric restriction over time. Where the stomach is stapled, the original staples must be removed and replaced. Suture-coupled fasteners, on the other hand, allow the surgeon to merely apply additional tension to the suture to keep the stomach walls together.

It may also be necessary to tension the suture during the initial gastric restriction procedure. While suture-coupled fasteners tend to be more advantageous than staples, as the surgeon is attaching the fasteners to the opposed walls of the stomach, slack or loops of excess suture can form. For the gastric restriction procedure to be successful, the suture must be tightly cinched to pull the gastric walls together so that the reduced volume of the patient's stomach can be maintained. If any slack or loose loops of suture are present, the stomach will expand and the restriction procedure will not be effective. Where additional tension is not effective to remove any slack or loops, it may be necessary to knot the excess suture to prevent it from loosening.

Accordingly, a need exists for methods and devices for tensioning a length of suture.

SUMMARY OF THE INVENTION

The present invention generally provides devices and methods for tensioning a length of suture. In one embodiment, a suture tensioning device is provided having a shaft, a knotting element, and a suture grasping member. The knotting element can be removably coupled to a distal end of the shaft, and it can be adapted to receive a suture and to lock to engage the suture. The suture grasping member can be movably coupled to the shaft, and it can be configured to grasp a suture and pull it through the knotting element to allow the knotting element to lock and engage the suture.

The suture grasping member can have a variety of configurations, but in one exemplary embodiment it can be slidably disposed within an inner lumen formed in the shaft and it can extend through at least a portion of the knotting element. The suture grasping member can include a hook formed on a distal end thereof and adapted to engage a length of suture.

The knotting element can also have a variety of configurations, but in one exemplary embodiment it can include an outer sleeve and an insert receivable within the outer sleeve for locking a suture therebetween. The insert can be sized to secure a suture by interference fit. For example, the insert can be compressible and the outer sleeve can be sized to compress the insert therein. The insert and outer sleeve can also include a locking mechanism formed therebetween and adapted to prevent the insert from backing out of the sleeve once received therein. The locking mechanism, for example, can include a flange formed on the insert and a complementary cam formed on the sleeve and adapted to engage the flange.

The device can also include features to allow the knotting element to removably mate to the shaft. In one aspect, a distal end of the shaft and a proximal end of the knotting element can include a mating element adapted to removably mate the knotting element to the shaft. The mating element can be, for example, at least one pin and at least one bore adapted to receive and engage the pin. The pin(s) can be sized such that it is held in the bore(s) by interference fit. Various techniques can be used to release the pin(s) from the bore(s).

The shaft can also have a variety of configurations, but in an exemplary embodiment it can include an actuator that is adapted to advance the insert into the outer sleeve of the knotting element to lock a suture therein. The actuator can include a rod that extends through an inner lumen of the shaft. In one embodiment, the distal end of the rod and a proximal end of the insert can include a mating element adapted to removably mate the insert to the rod. The mating element can be, for example, at least one pin and at least one bore adapted to receive and engage the pin. In a further embodiment, the pin(s) can be sized such that it is held in the bore(s) by interference fit.

In another aspect of the invention, a method for tensioning suture is provided and includes engaging a length of suture with a suture grasping member coupled to a shaft. The suture can have opposed ends extending through tissue. The suture grasping member is then retracted to pull the suture through a knotting element coupled to a distal end of the shaft to tension the suture relative to the tissue. A mechanism on the shaft can be actuated to lock the knotting element with the suture therein, and the knotting element can be released from the shaft. In an exemplary embodiment, the suture grasping member is advanced distally through at least a portion of the knotting element, and the suture is engaged with a hook formed on a distal end of the suture grasping member. In another aspect, actuating the knotting element can include advancing an insert into an outer sleeve of the knotting element to compress the insert and engage a suture extending therethrough. Releasing the knotting element can include releasing a proximal end of the insert from a distal end of a rod that extends through an inner lumen of the shaft. Releasing the knotting element can also include releasing a proximal end of the sleeve from a distal end of the shaft.

In yet another aspect of the invention, a method of reconditioning the suture tensioning device is provided and includes replacing or cleaning at least a portion of at least one of the shaft, knotting element, and suture grasping member. The method can further include disassembling at least a portion of the device before the step of replacing or cleaning. The method can also include reassembling at least a portion of the device after the step of replacing or cleaning.

BRIEF DESCRIPTION OF THE DRAWINGS

The invention will be more fully understood from the following detailed description taken in conjunction with the accompanying drawings, in which.

DETAILED DESCRIPTION OF THE INVENTION

Certain exemplary embodiments will now be described to provide an overall understanding of the principles, structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with features of other embodiments. Such modifications and variations are intended to be included within the scope of the present invention.

The present invention generally provides devices and methods for tensioning a length of suture. In an exemplary embodiment, a suture tensioning device is provided having a shaft and a suture grasping member movably coupled to the shaft. The device can be configured to removably couple to a knotting element for locking suture extending therethrough. In particular, the suture grasping member can be configured to grasp a suture and pull it through the knotting element to allow the knotting element to lock and engage the suture thereby tensioning the suture relative to tissue through which the suture extends. While the suture tensioning device can be used in any procedure in which it is desirable to tension suture, the suture tensioning device is particularly effective for use in tensioning slack or loops that have formed in sutures used to join opposed walls of the stomach during a gastric restriction procedure and/or for use in tensioning suture which has become loose or otherwise needs to be re-tensioned.

Figure 1A:
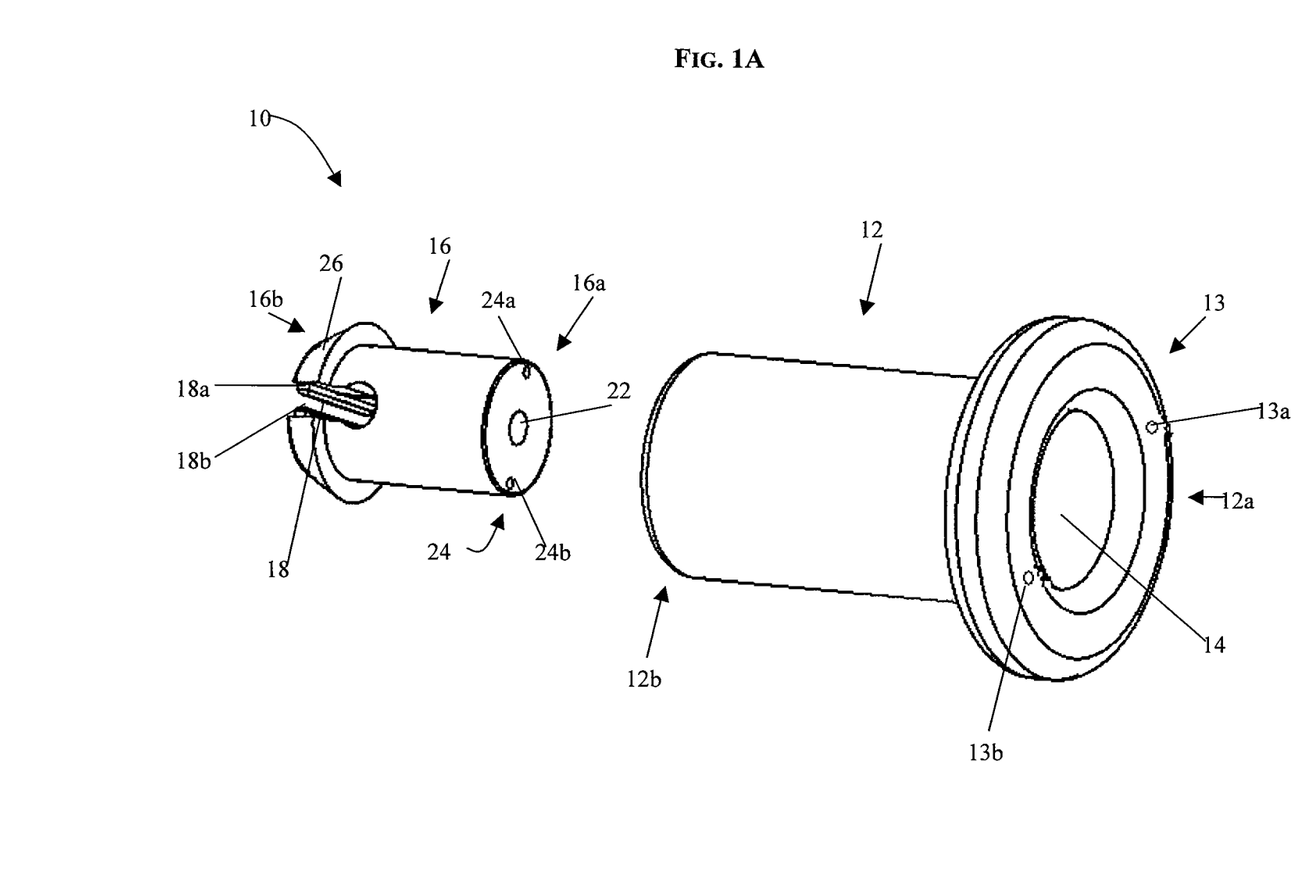
FIG. 1A is a perspective view of one embodiment of a knotting element having an insert and an outer sleeve.
Figure 1B:
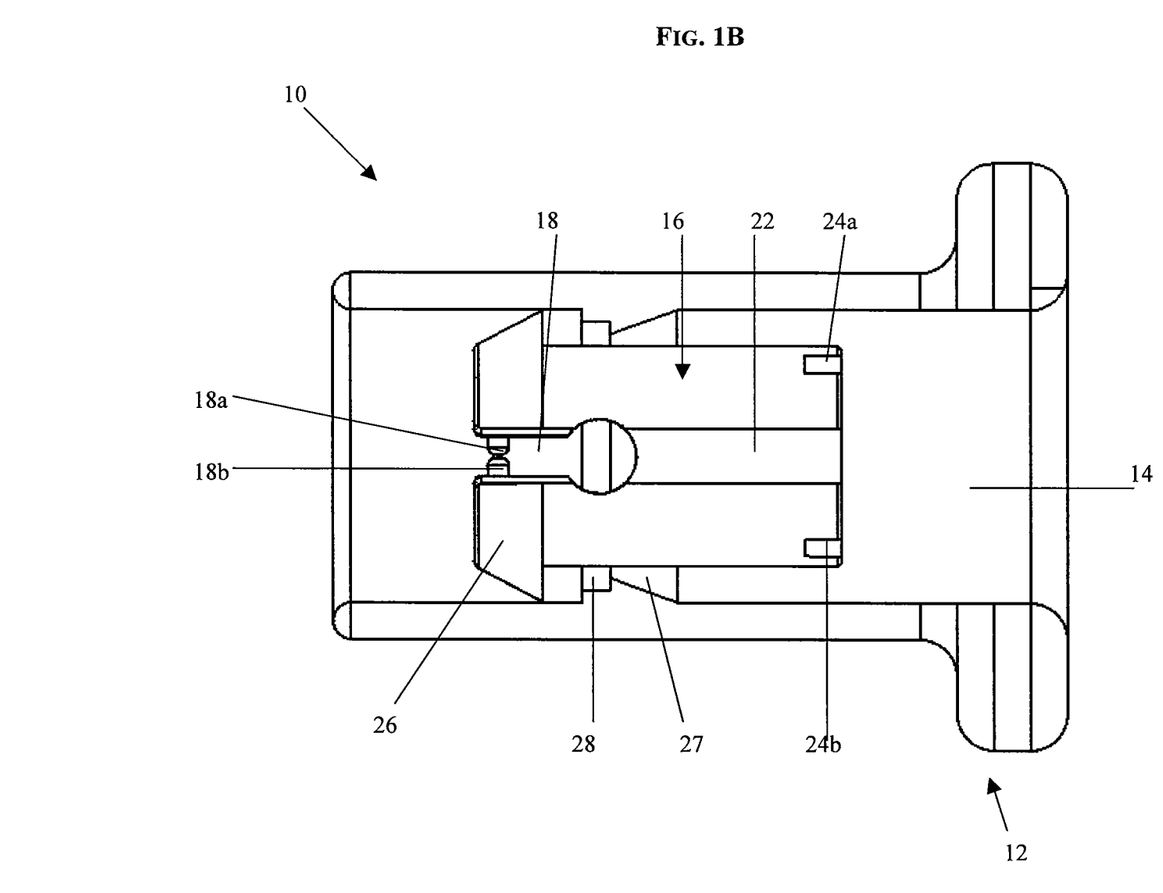
FIG. 1B is a cross-sectional view of the knotting element shown in FIG. 1 with the insert received within the outer sleeve.

The suture tensioning devices and methods disclosed herein can be used with any device or element known in the art that is effective to knot or lock a suture therein. By way of non-limiting example, FIGS. 1A and 1B illustrate one exemplary embodiment of a knotting element 10 that can be used with the suture tensioning devices and methods disclosed herein. As shown, the knotting element 10 includes an outer sleeve 12 and an insert 16 receivable within the outer sleeve 12. The outer sleeve 12 has a generally cylindrical shape with an inner lumen 14 extending between proximal and distal ends 12a, 12b thereof. The lumen 14 preferably has a size and shape that is effective to receive the insert 16 therein, and more preferably that is effective to compress at least a portion of the insert 16 to lock a suture extending therethrough, as will be discussed below. The insert 16 can also have a generally cylindrical shape such that it can be slidably received within the lumen 14 of the sleeve 12. An inner lumen 22 can extend between proximal and distal ends 16a, 16b of the insert 16 for receiving a suture therethrough. As shown in FIGS. 1A and 1B, the insert 16 can also include a suture-receiving cavity 18 formed in the distal end thereof. The cavity 18 is effective to separate or split the distal end of the insert 16 such that the opposed ends of the insert 16 can be compressed toward one another. In an exemplary embodiment, at least a portion of the lumen 14 has an inner diameter that is smaller than an outer diameter of a compressible portion of the insert 16 to compress the insert 16 when it is received therein. As shown in FIG. 1B, a distal portion of the lumen 14 in the sleeve 12 has a reduced diameter that is effective to compress the distal portion of the insert 16 around the suture receiving cavity 18. As a result, a suture extending through the suture receiving cavity 18 will be engaged therein. As further shown in FIG. 1A, the suture receiving cavity 18 can include opposed ridges 18a, 18b formed therein and extending transverse to the lumen 22 in the insert 16. The ridges 18a, 18b can facilitate engagement of a suture positioned therebetween and pulled into the lumen 22. A person skilled in the art will appreciate that a variety of other techniques can be used to engage a suture within the insert 16 or between the insert 16 and the sleeve 12.

As further shown in FIGS. 1A and 1B, the knotting element 10 can also include a locking mechanism formed between the outer sleeve 12 and the insert 16 and adapted to prevent the insert 16 from backing out of the sleeve 12 once received therein. While the locking mechanism can have various configurations, in the illustrated embodiment the distal end 16b of the insert 16 includes a flange 26 formed thereon, and the inner lumen 14 of the sleeve includes a complementary cam 27 formed thereon and adapted to engage the flange 26 when the insert 16 is slid into the sleeve 12. In particular, as the flange 26 slides past the cam 27, the flange 26 can engage and abut against a lip 28 of the cam 27. The lip 28 will lock the insert 16 within the sleeve 12 thereby preventing the insert 16 from backing out, i.e., sliding proximally within the sleeve 12.

Figure 2A:
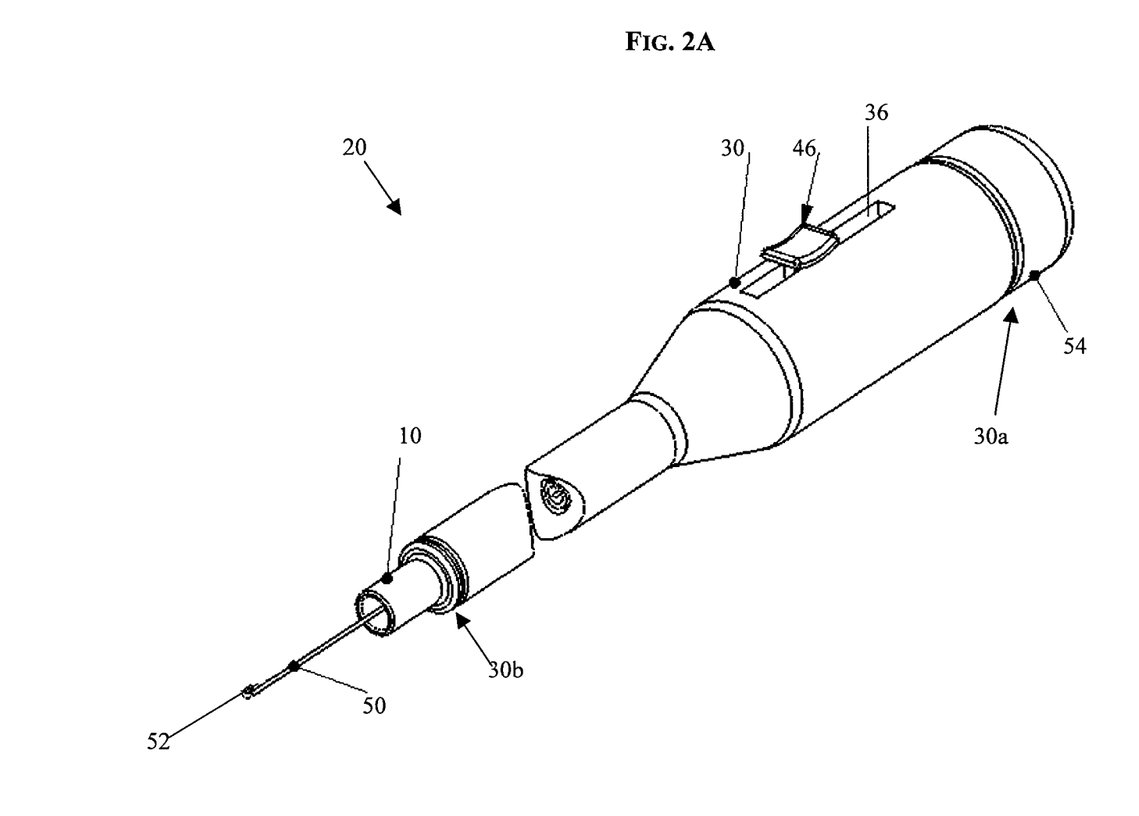
FIG. 2A is a perspective view of one embodiment of a suture tensioning device showing the knotting element of FIGS. 1A and 1B coupled thereto.
Figure 2B:
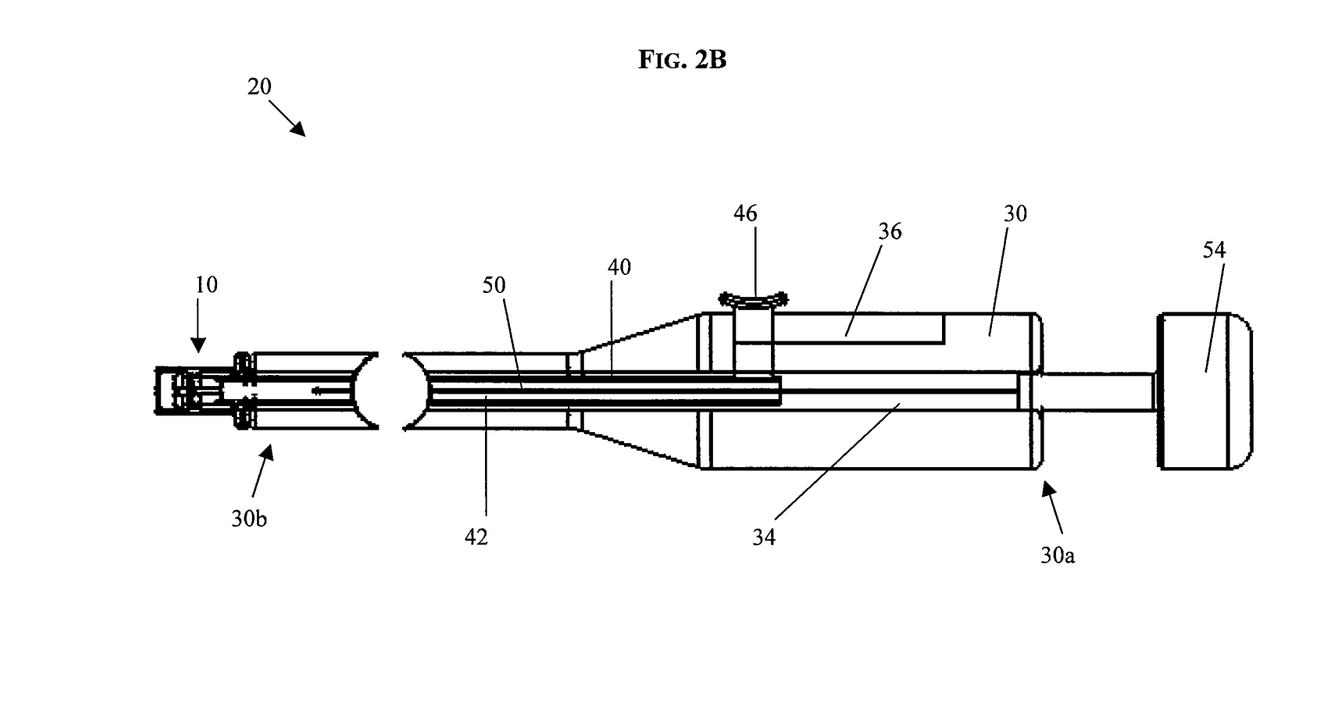
FIG. 2B is a cross-sectional view of the suture tensioning device and knotting element shown in FIG. 2A.

As previously indicated, the present invention provides a suture tensioning device for engaging and pulling a length of suture through a knotting element, such as knotting element 10 shown in FIGS. 1A and 1B. FIGS. 2A and 2B illustrate one exemplary embodiment of a suture tensioning device 20 having a shaft 30 and a suture grasping member 50 movably coupled to the shaft 30. A distal end 30b of the shaft 30 can couple to the knotting element 10, and the suture grasping member 50 is configured to grasp a suture and pull it through the knotting element 10 to allow the knotting element 10 to lock and engage the suture therein. The device 20 can also include an actuation mechanism 46 formed on the shaft 30 that can be actuated to lock the knotting element 10 with the suture therein. The device 20 can also include features to release the knotting element 10.

Figure 3:
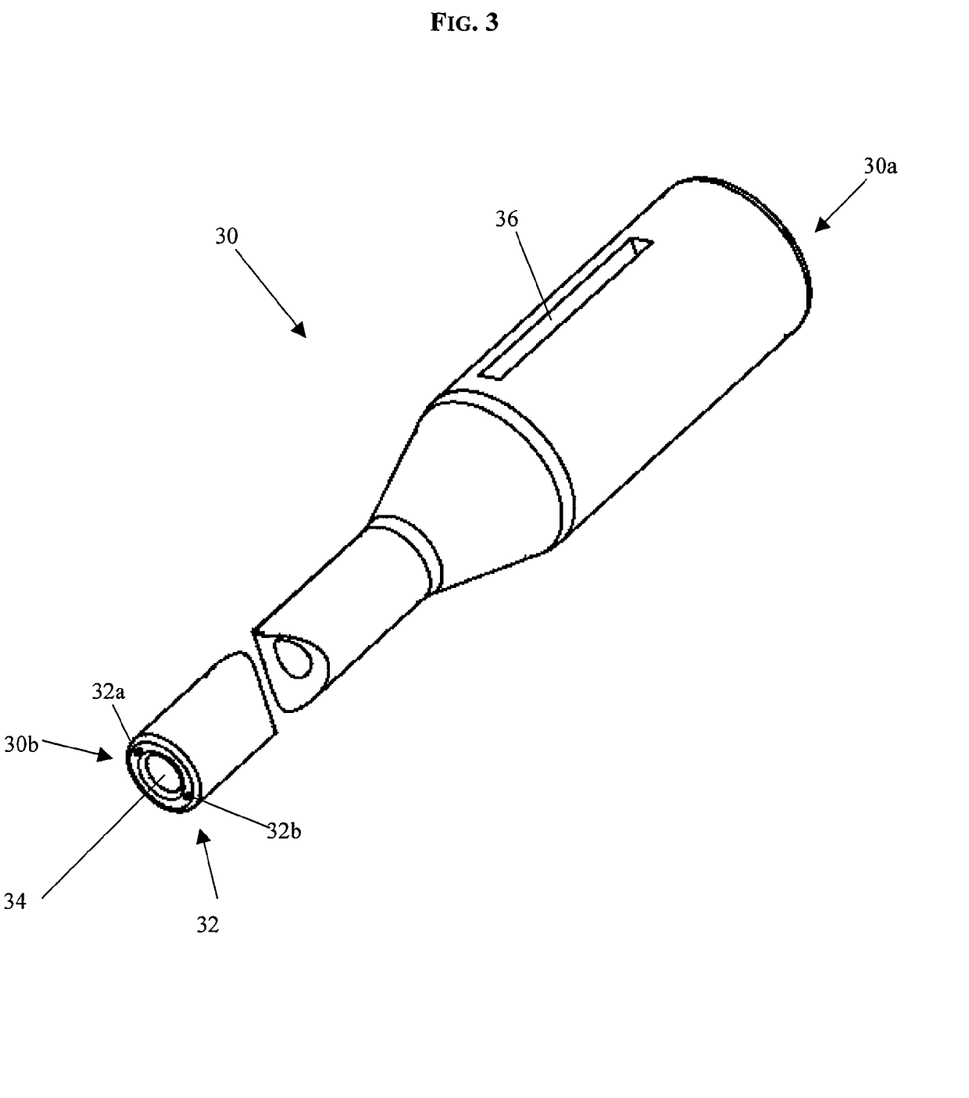
FIG. 3 is a perspective view of a shaft of the suture tensioning device shown in FIG. 2A.

The shaft 30 of the device 10 is shown in more detail in FIG. 3. While the shaft can have any shape and size, in the illustrated embodiment the shaft 30 has a generally elongate body in the form of a housing having proximal and distal ends 30a, 30b. The proximal end 30a of the shaft 30 can be in the form of, or can include, a handle for grasping and manipulating the device. The distal end 30b of the shaft 30 can removably mate to the knotting element, as will be explained below in more detail. An inner lumen 34 can extend between the proximal and distal ends 30a, 30b of the shaft 30 for slidably receiving the suture grasping member 50, as shown in FIG. 2B. The length of the shaft 30 can vary depending on the intended use. For example, in one exemplary embodiment, the length can be configured for endoscopic use, and all or portions of the shaft 30 can be flexible to accommodate an endoscopic procedure.

As indicated above, the distal end 30b of the shaft 30 is preferably adapted to removably mate to the knotting element 10. While various mating techniques can be used, in one exemplary embodiment the shaft 30 can include a mating element formed on the distal end thereof and adapted to removably mate to a complementary mating element formed on the knotting element 10. In the illustrated embodiment, the distal end 30b of the shaft 30 includes first and second pins 32a, 32b formed thereon and adapted to be slidably received within first and second bores 13a, 13b formed in the proximal end of the outer sleeve 12 of the knotting element 10. The pin(s) and bore(s) can have various shapes and sizes, and they can be effective to mate to one another using a snap-fit, interference fit, or other engagement technique. Exemplary pin shapes include cylindrical and hexagonal. In use, the mating element is effective to secure the sleeve 12 to the shaft 30 during the suture tensioning procedure. A person skilled in the art will appreciate that other available mating techniques can be used including, for example, a magnetic engagement, a twist lock connection, or a threaded mating connection formed between the sleeve 12 of the knotting element 10 and the shaft 30.

Figure 4:
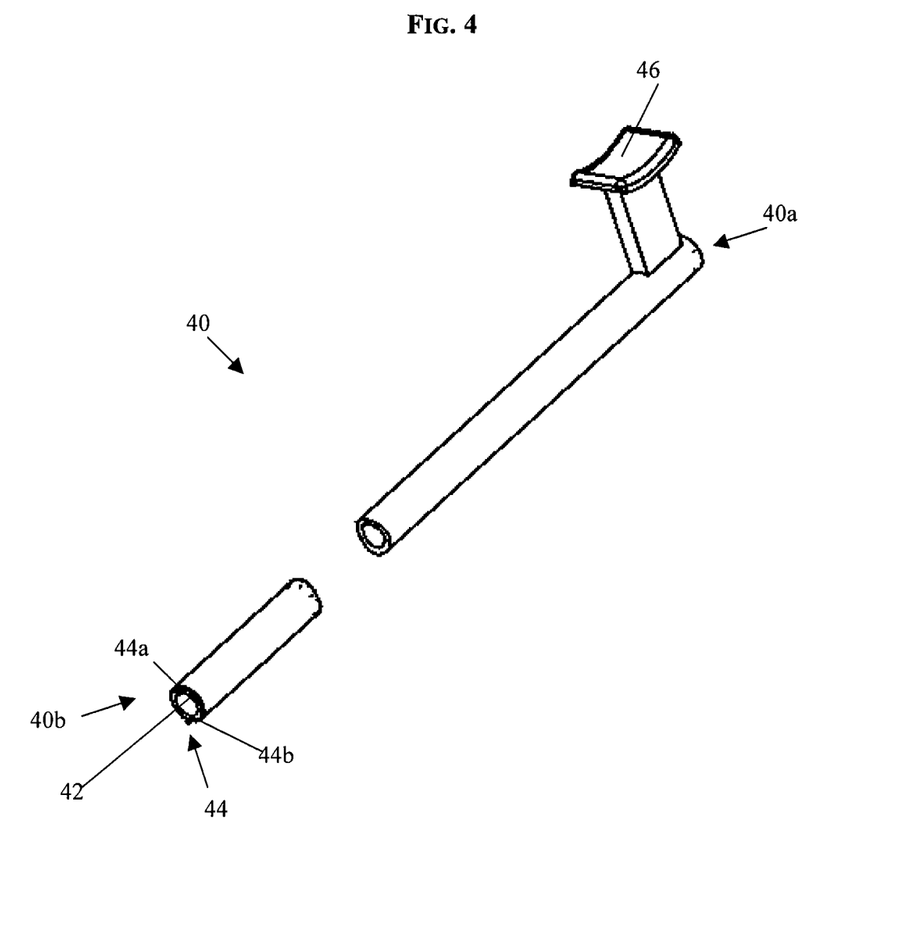
FIG. 4 is a perspective view of an actuator of the suture tensioning device shown in FIG. 2A.

As shown in FIG. 4, the shaft 30 can also include an actuator adapted to advance the insert 16 into the sleeve 12 of the knotting element 10 to thereby lock a suture within the knotting element 10. In one embodiment, the actuator can be in the form of a rod 40 that extends through the inner lumen 34 of the shaft 30. The rod 40 can have an inner lumen 42 extending from a proximal end 40a to a distal end 40b thereof for receiving the suture grasping member, which will be described below in more detail. The distal end 40b of the rod 40 can abut against the insert 16 of the knotting element 10 to move the insert 16. In an exemplary embodiment, the rod 40 can include a mating element formed on the distal end 40b thereof and adapted to removably mate to a complementary mating element formed on the insert 16 of the knotting element 10. While the mating element can have a variety of configurations, in one embodiment, the mating elements 24, 44 associated with the insert 16 and the rod 40 can be similar to the mating elements 13, 30 described above. For example, as shown in FIG. 4, the distal end 40b of the rod 40 includes first and second pins 44a, 44b formed thereon and adapted to be slidably received within first and second bores 24a, 24b formed in the proximal end of the insert 16 of the knotting element 10. The pin(s) and bore(s) can have various shapes and sizes, and they can be effective to mate to one another using a snap-fit, interference fit, or other engagement technique. Exemplary pin shapes include cylindrical and hexagonal. As with the mating element described above, other available mating techniques can be used including, for example, a magnetic engagement, a twist lock connection, or a threaded mating connection formed between the insert 16 of the knotting element 10 and the rod 40. In use, the rod 40 can be slidably movable within the inner lumen 34 of the shaft 30 to advance the insert 16 into the sleeve 12 of the knotting element 10. Various techniques can be used to move the rod 40 relative to the shaft 30 including, for example, a handle, knob, or lever. In the embodiment shown in FIG. 4, a handle 46 is disposed on the proximal end 40a of the rod 40 and is positioned within a slot 36 formed in the shaft 30. The handle 46 on the rod 40 can slidably move between a proximal position in which it retains the insert 16 within the shaft 30, and a distal position in which the insert 16 is advanced into the sleeve 12. Once the insert 16 is locked within the sleeve 12, as described above, the rod 40 can be released from the insert 16 by retracting the rod 40. The locking mechanism will prevent the insert from being retracted with the rod 40.

Figure 5:
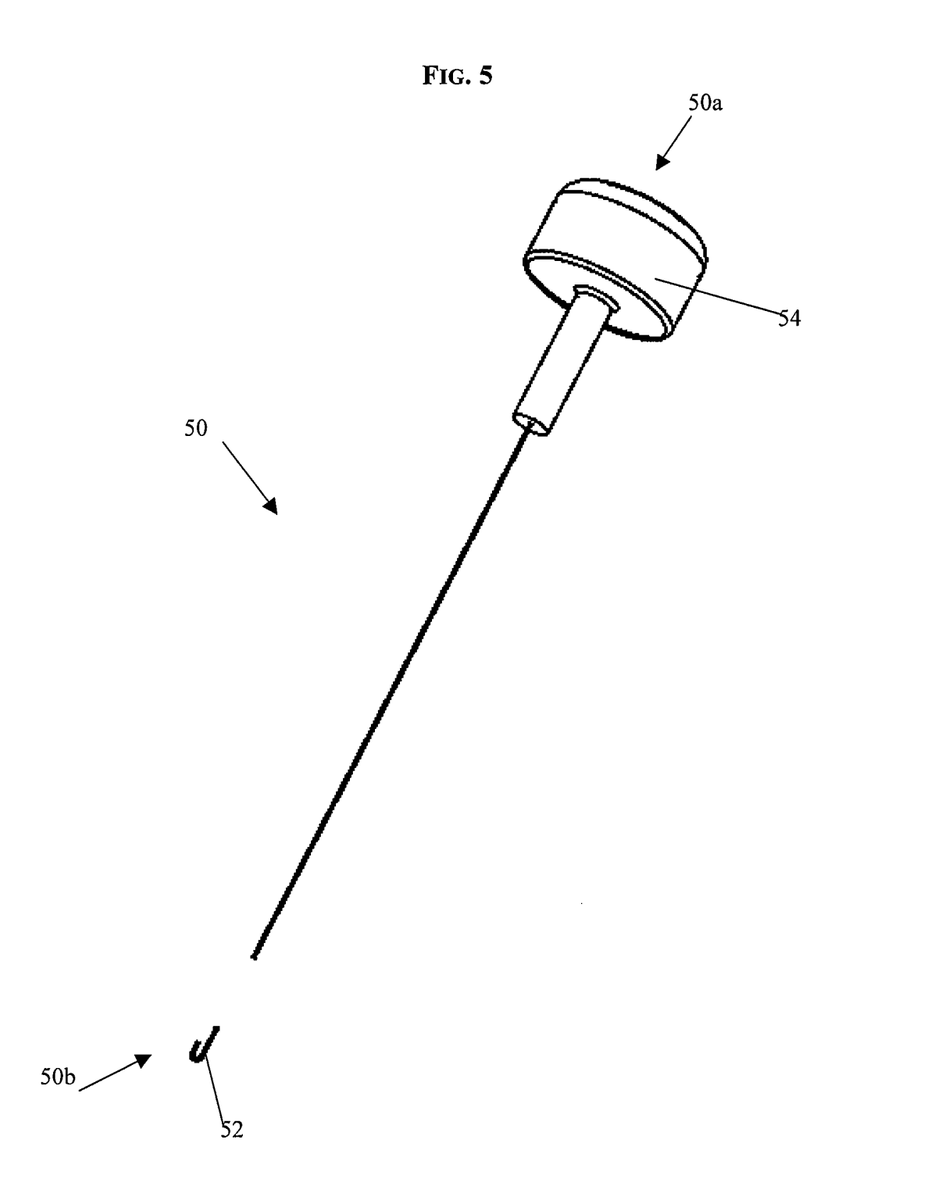
FIG. 5 is a perspective view of a suture grasping member of the suture tensioning device shown in FIG. 2A.

As shown in FIGS. 2A, 2B and 5, the tensioning device 20 can also include a suture grasping member 50 that is adapted to grasp a suture and pull the suture through the knotting element. The suture grasping member 50 can have virtually any shape and size, but in one exemplary embodiment it has a generally elongate configuration with a proximal end 50a extending from the proximal end 30a of the shaft 30 and a distal end 50b extending through the shaft 30, rod 40, and knotting element 10. The proximal end 50a of the suture grasping member 50 can be movably coupled to the shaft 30, and the distal most end 50b of the suture grasping member 50 can include an engagement mechanism, such as a hook 52, formed thereon for engaging a suture. Other techniques, such as grasping devices, can be used to engage a suture. As further shown in FIGS. 2A, 2B, and 5, a handle can be disposed at the proximal end 50a of the suture grasping member 50 for advancing and retracting the member between a distal position in which the distal end 50b of the suture grasping member 50 extends beyond the distal end 30b of the shaft 30 to grasp a length of suture 60, and a proximal position in which the distal end 50b of the suture grasping member 50 is pulled through the knotting element 10. In an exemplary embodiment, the suture grasping member 50 is formed from a thin wire made of a rigid or semi-rigid material, and it has an elongate length to facilitate use in an endoscopic procedure.

Figure 6A:
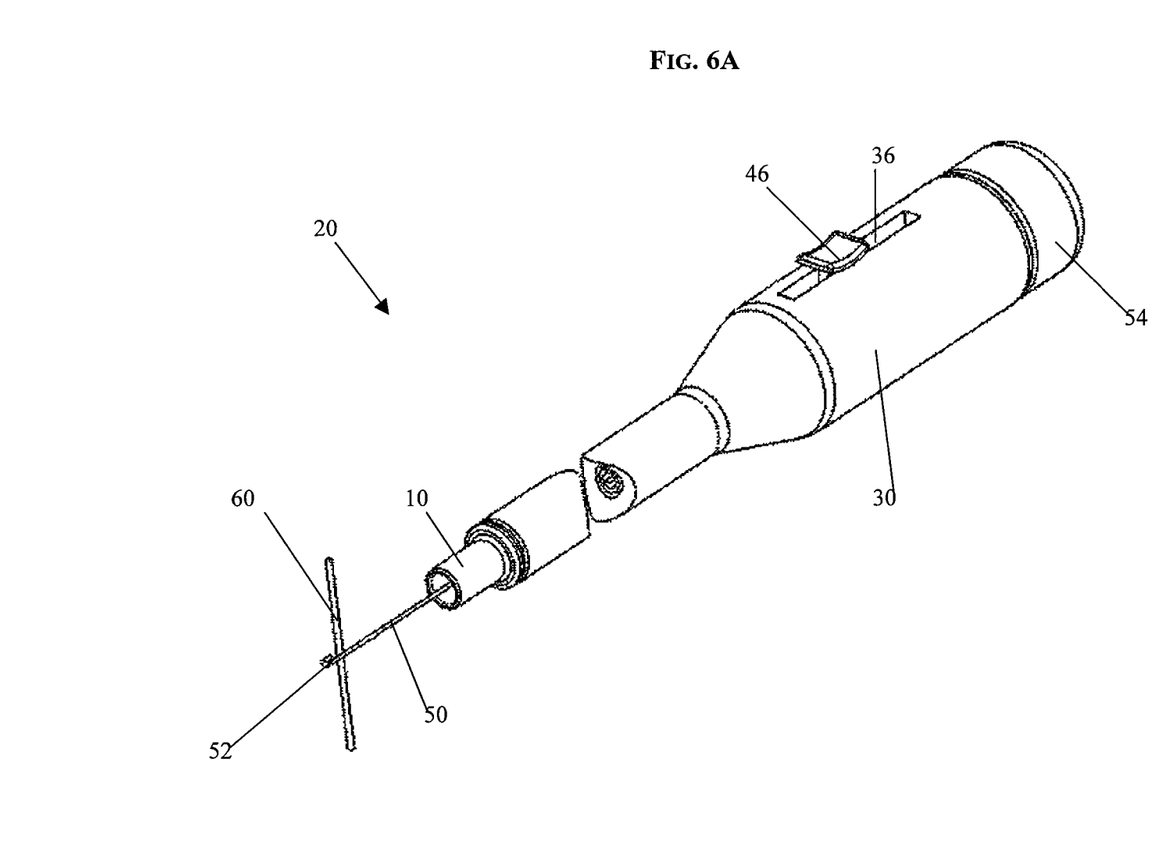
FIG. 6A is a perspective view of the suture tensioning device shown in FIG. 2A showing the suture grasping member extending through the knotting element and engaging a length of suture.
Figure 6B:
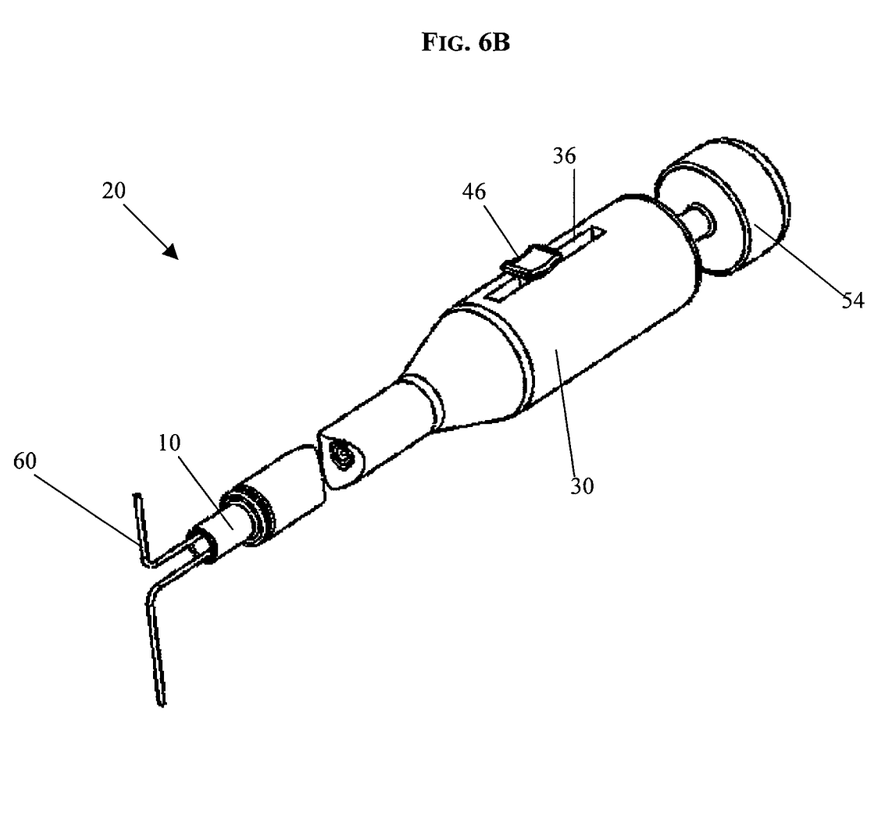
FIG. 6B is a perspective view of the suture tensioning device shown in FIG. 6A showing the suture grasping member in a retracted position to pull the suture through the knotting element.
Figure 6C:
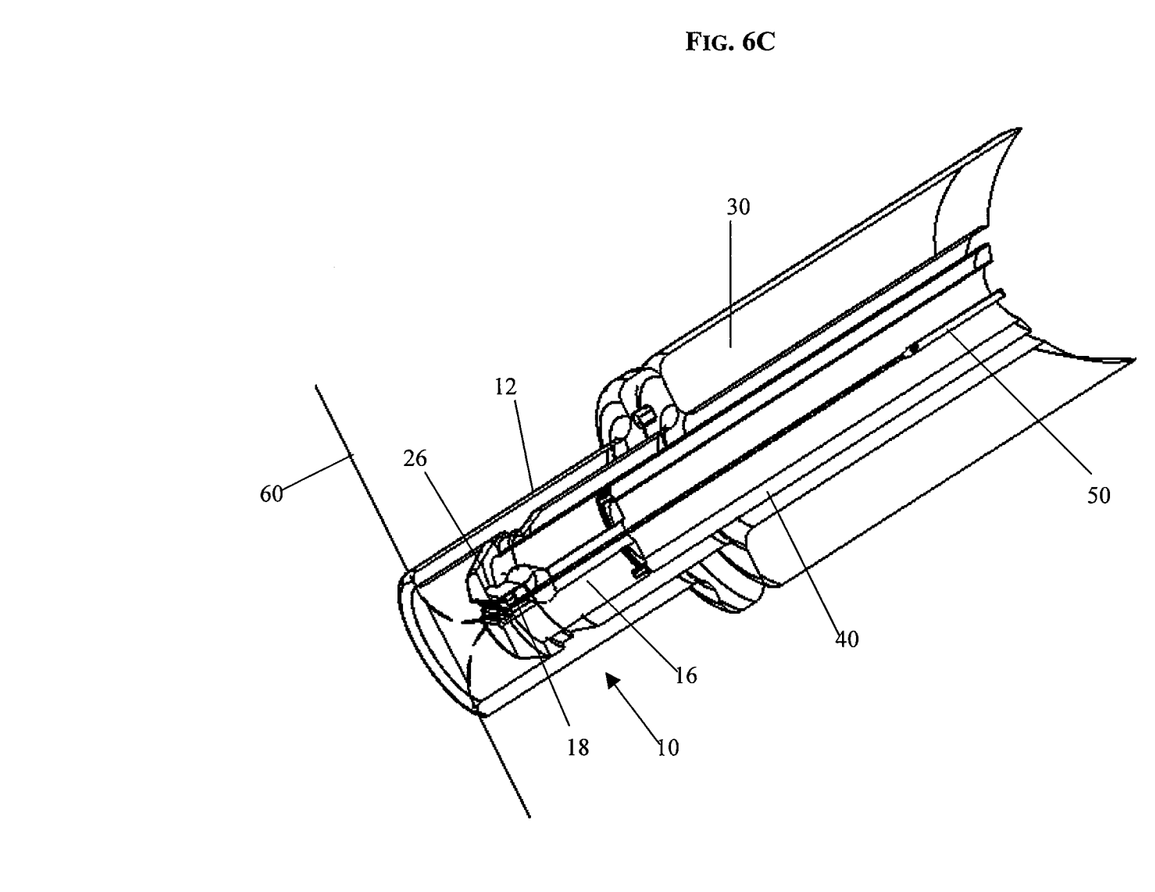
FIG. 6C is a cross-sectional view of a distal portion of the suture tensioning device and the knotting element shown in FIG. 6B showing a suture locked in the knotting element.

FIGS. 6A-6D illustrate the device 20 in use for tensioning and locking a length of suture having opposed ends extending through tissue (not shown). The device 20 can be inserted into the body, for example, through an access port or, in a preferred embodiment, endoscopically (i.e., through a natural orifice such as the esophagus). The device 20 can be used in conjunction with an endoscope or it can optionally include on-board image gathering and/or display optics to facilitate endoscopic viewing. Once the device 20 is positioned in the body proximate to suture 60 to be tensioned, the suture grasping member 50 can be advanced such that a distal portion of the member 50 extends distally from the distal end 30b of the shaft 30 and from the knotting element 10. As shown in FIG. 6A, the suture grasping member 50 can be manipulated to engage the suture 60 using the hook 52 formed on the distal end 50b of the member 50. After engaging the suture 60, the suture grasping member 50 can be retracted by pulling the handle 54 on the proximal end of the suture grasping member 50 to pull the suture 60 through the knotting element 10 thereby tensioning the suture 60 as shown in FIG. 6B. The tension can be adjusted by moving the suture grasping member 50 to a desired position. The suture 60 can then be locked within the knotting element 10 by advancing the rod 40 distally to cause the insert 16 to be advanced into and compressed by the sleeve 12, as shown in FIG. 6C. As the insert 16 is slidably received by the sleeve 12, the flange 26 formed on the insert 16 slides over the cam 27 formed on the sleeve 12. Once the flange 26 has cleared the cam 27, the flange 26 engages the lip 28 adjacent to the cam 27 and the insert 16 is prevented from backing out. The reduced diameter region in the lumen 14 will compress the insert 16 to lock the suture therein.

Figure 6D:
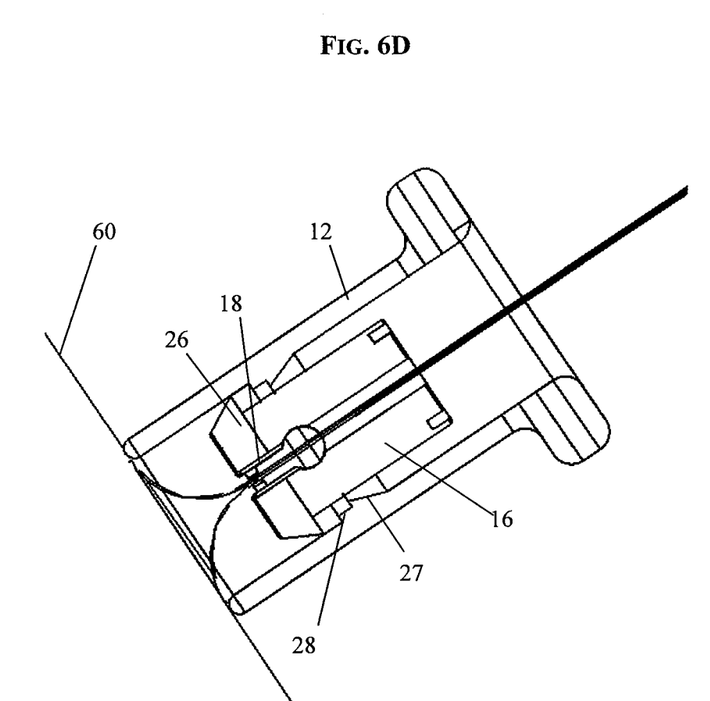
FIG. 6D is a cross-sectional view of the knotting element of FIG. 6C detached from the suture tensioning device.

After locking the suture 60 within the knotting element 10, the knotting element 10 can be released from the device 20. In one exemplary embodiment, the insert 16 can be released from the rod 40 by retracting the rod 40. As described above, as the rod 40 is retracted, the lip 28 on the sleeve 12 will engage the flange 26 on the insert 16 to retain the insert 16 within the sleeve 12. The sleeve 12 can be released from the shaft 30 by, for example, retracting the pins 32a, 32b on the distal end 30b of the shaft 30 using an actuating mechanism (not shown) that extends through the shaft and is coupled to or integrally formed with the pins. In other embodiments, the rod 40 can be rotated after it is detached from the insert 16 such that the pins on the rod 40 are offset from the bores in the insert 16. The rod 40 can then be moved distally to push the knotting element 10 off of the distal end of the shaft 30. In yet another embodiment, the sleeve 12 can be threadably released from the shaft 30. A person skilled in the art will appreciate that a variety of other techniques can be used to release the knotting element.

In another exemplary embodiment, the suture tensioning device 20, or portions thereof, can be designed to be disposed of after a single use, or it can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the suture tensioning device and its components shown in FIGS. 1A-5 can be reconditioned after the device has been used in a medical procedure. The device can be disassembled, and any number of the particular pieces (e.g., the shaft 30, the rod 40, the knotting element 10, or the suture grasping member 50) can be selectively replaced or removed in any combination. For instance, the knotting element can be replaced by a new knotting element, while the remaining pieces are sterilized for reuse. Replacement of pieces can also include replacement of portions of particular elements. Upon cleaning and/or replacement of particular parts, the device can be reassembled for subsequent use either at a reconditioning facility, or by a surgical team immediately prior to a surgical procedure. Those skilled in the art will appreciate that reconditioning of a suture tensioning device can utilize a variety of techniques for disassembly, cleaning/replacement, and reassembly. Use of such techniques, and the resulting reconditioned suture tensioning device, are all within the scope of the present application.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present invention. As well, one skilled in the art will appreciate further features and advantages of the invention based on the above-described embodiments. Accordingly, the invention is not to be limited by what has been particularly shown and described, except as indicated by the appended claims.

What is claimed is:

1. A suture tensioning device, comprising:
    a shaft having proximal and distal ends and an inner lumen extending therethrough;
    a knotting element and adapted to receive a suture and to lock to engage the suture, the knotting element including an outer sleeve removably coupled to the distal end of the shaft and an insert receivable within an inner lumen of the outer sleeve to lock a suture therein;
    an elongate tubular actuator extending through an inner lumen of the shaft and being slidable between a proximal position in which the actuator retains the insert within the inner lumen of the shaft and a distal position in which the actuator advances the insert into the inner lumen of the sleeve; and
    a suture grasping member movably coupled to the shaft and extending through the inner lumen of the actuator, through the inner lumen of the outer sleeve, and through an inner lumen of the insert such that a distal end of the suture grasping member is positioned distally beyond the knotting element such that the distal end of the suture grasping element can grasp a suture positioned distally beyond the knotting element and pull the suture in a proximal direction through the inner lumen of the outer sleeve and the inner lumen of the insert to position the distal end of the suture grasping element proximal to the knotting element, and to allow the knotting element to lock and engage the suture.

2. The device of claim 1, wherein the suture grasping member is slidably disposed within the inner lumen formed in the shaft and extends through at least a portion of the knotting element.

3. The device of claim 1, wherein the suture grasping member includes a hook formed on a distal end thereof and adapted to engage a length of suture.

4. The device of claim 1, wherein the distal end of the shaft and a proximal end of the outer sleeve include a mating element adapted to removably mate the outer sleeve to the shaft.

5. The device of claim 4, wherein the mating element comprises at least one pin and at least one bore adapted to receive and engage the pin.

6. The device of claim 5, wherein the at least one pin is sized to be held in the at least one bore by interference fit.

7. The device of claim 1, wherein the insert is sized to secure a suture by interference fit within the outer sleeve.

8. The device of claim 1, wherein the insert is compressible, and wherein the outer sleeve is sized to compress the insert therein.

9. The device of claim 1, wherein the elongate tubular actuator is rigid.

10. The device of claim 9, wherein a distal end of the elongate tubular actuator and the proximal end of the insert include a mating element adapted to removably mate the insert to the elongate tubular actuator.

11. The device of claim 10, wherein the mating element comprises at least one pin and at least one bore adapted to receive and engage the pin.

12. The device of claim 11, wherein the at least one pin is sized to be held in the at least one bore by interference fit.

13. The device of claim 1, wherein the insert has a cavity formed in the distal end thereof such that opposed ends at the distal end of the insert can be compressed toward one another.

14. The device of claim 1, wherein the insert and knotting element include a locking mechanism formed therebetween and adapted to prevent the insert from backing out of the sleeve once received therein, the locking mechanism including a flange formed on the insert and a complementary cam formed on the sleeve and adapted to engage the flange.

15. The device of claim 1, wherein a proximal-most end of the actuator cannot extend proximally beyond the proximal end of the shaft.

16. The device of claim 1, wherein a handle is disposed on a proximal end of the actuator, the handle being slidable to move the actuator between the proximal and distal positions.

17. The device of claim 16, wherein the handle is positioned within a slot formed in a sidewall of the shaft.

18. A suture tensioning device, comprising:
a shaft having an inner lumen;
a knotting element removably coupled to a distal end of the shaft, the knotting element including a first member having an inner lumen and a second member having an inner lumen and being receivable within the inner lumen of the first member;
an actuator having an inner lumen and extending through the inner lumen of the shaft, the actuator being configured to advance the second member within the inner lumen of the first member; and
a suture grasping member slidably disposed in the inner lumens of the actuator, the first member, the second member, and the shaft such that a distal end of the suture grasping member is positioned distally beyond the actuator, the first and second members, and the shaft, the distal end of the suture grasping member being configured to grasp a suture positioned distally beyond the actuator, the first and second members, and the shaft, and to proximally advance through the inner lumens of the actuator, the shaft, the first member, and the second member to pull the suture grasped by the suture grasping member in a proximal direction through the knotting element, wherein the suture grasping member is configured to distally advance through the inner lumens of the actuator and the first and second members and extend distally from a distal end of the knotting element prior to grasping a suture.

19. The device of claim 18, wherein the actuator is configured to lock the suture grasped by the suture grasping member within the knotting element by advancing the second member into the first member after the suture grasping member has pulled the suture grasped by the suture grasping member through the knotting element.

20. The device of claim 18, wherein the first member has a cam formed thereon and the second member has a flange formed thereon, the flange being adapted to engage the cam to prevent the second member from backing out of the first member once received therein.

21. The device of claim 18, wherein a proximal-most end of the actuator cannot extend proximally beyond a proximal end of the shaft.

22. The device of claim 18, wherein a handle is disposed on a proximal end of the actuator, the handle being slidable to move the actuator between a proximal position in which the actuator retains the second member within the inner lumen of the shaft and a distal position in which the second member is advanced into the first member.

23. The device of claim 22, wherein the handle is positioned within a slot formed in a sidewall of the shaft.

* * * * *